United States Patent [19]

Nathan et al.

[11] Patent Number: 5,001,169

[45] Date of Patent: Mar. 19, 1991

[54] INDUCTIVE COLLAGEN-BASED BONE REPAIR PREPARATIONS

[75] Inventors: Ranga Nathan, Newark; Saeid Seyedin, Mountain View; Karl Piez, Menlo Park; Hanne Bentz, Palo Alto, all of Calif.

[73] Assignee: Collagen Corporation, Palo Alto, Calif.

[21] Appl. No.: 816,268

[22] Filed: Jan. 6, 1986

Related U.S. Application Data

[63] Continuation-in-part of Ser. No. 664,158, Oct. 24, 1984, Pat. No. 4,563,350.

[51] Int. Cl.$^5$ .................... A61K 35/32; A61L 27/00
[52] U.S. Cl. .................... 523/113; 424/423; 106/161; 514/21; 514/801; 623/11; 623/16
[58] Field of Search ............. 523/113; 530/840, 350, 530/356, 399; 623/16, 11; 424/95, 423; 106/161; 514/801, 21

[56] References Cited

U.S. PATENT DOCUMENTS

| | | | |
|---|---|---|---|
| 4,294,753 | 10/1981 | Urist | 424/95 |
| 4,394,370 | 7/1983 | Jefferies | 424/15 |
| 4,430,760 | 2/1984 | Smestad | 3/1.9 |
| 4,434,094 | 2/1984 | Seyedin | 424/95 |
| 4,440,750 | 4/1984 | Glowacki | 424/95 |
| 4,445,256 | 6/1984 | Urist | 424/95 |
| 4,596,574 | 6/1986 | Urist | 623/16 |

FOREIGN PATENT DOCUMENTS

| | | |
|---|---|---|
| 0182483 | 5/1986 | European Pat. Off. . |
| 0121976 | 7/1986 | European Pat. Off. . |
| 0206801 | 12/1986 | European Pat. Off. . |
| 0243178 | 10/1987 | European Pat. Off. . |
| 0270254 | 11/1987 | European Pat. Off. . |
| 0197693 | 12/1987 | European Pat. Off. . |
| 2564732 | 11/1985 | France . |

OTHER PUBLICATIONS

Reddi, A. H. et al, *Proc. Nat. Acad. Sci., U.S.A.*, 69:1601–1605 (1972).
Urist, M. R. et al, *Proc. Natl. Acad. Sci., U.S.A.*, 81:371–375 (1984).
Urist, M. R. et al, *Science*, 220:680–686 (1983).
Urist, M. R. et al, *Clin. Ortho. and Related Res.*, 162:219–232 (1982).
Urist et al, "Solubilized and Insolubilized Bone Morphogenetic Protein", (*Proc. Nat. Acad. Sci., U.S.A.*) vol. 76, No. 4, pp. 1828–1832, Apr. 1979.
Termine et al, "Mineral and Collagen-Binding Proteins of Fetal Calf Bone", (*Journal of Biological Chemistry*). vol. 221, No. 20, pp. 10403–10408, 1981.

*Primary Examiner*—Nathan M. Nutter
*Attorney, Agent, or Firm*—Irell & Manella

[57] ABSTRACT

A composition suitable for inductive bone implants is disclosed. The composition comprises a purified form of osteogenic factor in admixture with a carrier having a percentage of mineral carrier. The resulting implants are sufficiently hypoimmunogenic to be effective when implanted in xenogeneic hosts.

11 Claims, 5 Drawing Sheets

14 DAYS

| IMPLANT | CARTILAGE INDUCTION | BONE FORMATION | INFLAMMATION |
|---|---|---|---|
| NFC / CERAMIC | 0 | 0 | 2 – 3 + |
| OFE / NFC / CERAMIC | 2 + | 3 – 4 + | 1 + |
| FC / CERAMIC | 0 | 0 | 1 – 2 + |
| OFE / FC / CERAMIC | TRACE | 1 – 3 + | 1 + |
| R - DBP | TRACE – 4 + | 1 – 3 + | 0 – 1 + |

SCALE FOR BONE FORMATION AND INFLAMMATION = 0 – 5 +

FIG. 3A

28 DAYS

| IMPLANT | CARTILAGE INDUCTION | BONE FORMATION | INFLAMMATION |
|---|---|---|---|
| NFC / CERAMIC | 0 | 0 | 2 + |
| OFE / NFC / CERAMIC | TRACE | 4 + | 0 – 1 + |
| FC / CERAMIC | 0 | 0 | 0 – 1 + |
| OFE / FC / CERAMIC | TRACE | TRACE – 4 + | 1 + |
| R - DBP | TRACE – 4 + | 2 – 5 + | 0 – 1 + |

SCALE FOR BONE FORMATION AND INFLAMMATION = 0 – 5 +

HISTOLOGICAL EVALUATION

FIG. 3B

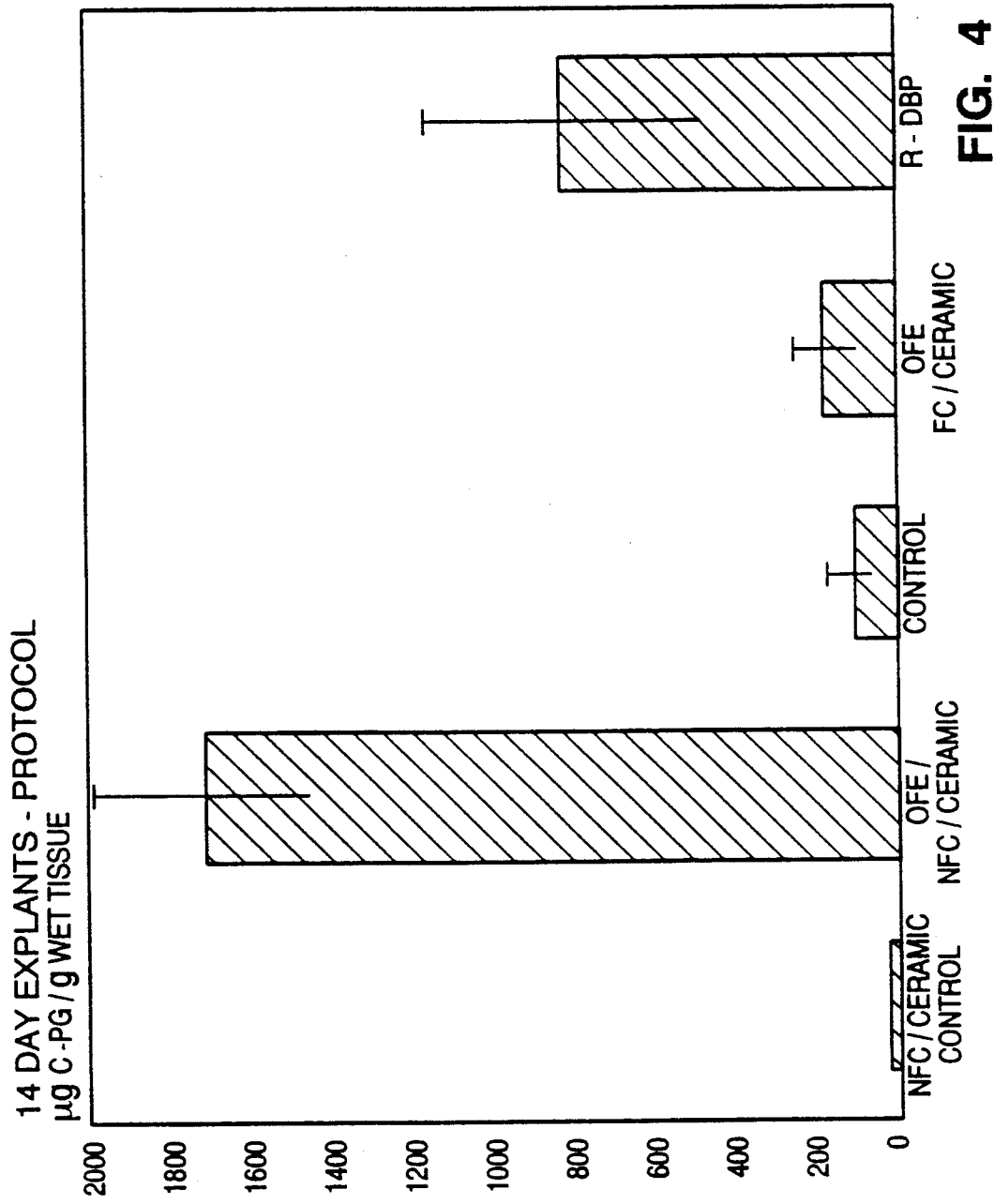

INDUCTIVE COLLAGEN-BASED BONE REPAIR PREPARATIONS

This is a continuation-in-part of U.S. patent application Ser. No. 664,158, filed 24 Oct. 1984 and now U.S. Pat. No. 4,563,350.

TECHNICAL FIELD

The present invention relates to bone repair materials. More specifically, it relates to mineral and collagen containing supports for chondrogenic/osteogenic proteins.

BACKGROUND ART

Repair of damaged or defective bone which involves more than the healing of a simple fracture has used three approaches to supply the required bone tissue: In the simplest approach, a prosthesis, intended to be permanent, is placed as a substitute for missing bone, and provisions made to integrate the prosthesis into the skeletal structure of the host. Such bone replacements may be made of artificial materials such as biocompatible metals, or may constitute allografts derived from bone structure elsewhere in the subject. A slightly more complex approach has been to provide a matrix to support ingrowth of bone from surrounding healthy tissue with subsequent possible resorption of the matrix. A third approach has been to supply both a matrix and an osteogenic factor which biochemically induces the ingrowth with or without a cartilagenous intermediate.

The history of development of the last two approaches, often called, respectively, "conductive" and "inductive" repair, shows continuing progress toward biologically derived materials which are of sufficiently low immunogenicity to enable them to function without unfavorable side effects. Since collagen is the major organic component of bone, its use as, or in, a matrix for subsequent deposit of the mineral bone component by adjacent cells has been extensive. However, collagen per se contains "telopeptide" units which are immunogenic, and a great improvement with respect to collagen for use in such matrix construction has been the use of "atelopeptide" collagen. Removal or partial removal of the telopeptides and consequent suppression of the immunogenic response may be important as this improves the performance in conductive bone repair of collagen derived from species foreign to that of the host—i.e., using "xenogeneic" collagen. For human recipients, this is significant because porcine, bovine, or other mammalian sources may be used for the preparation, rather than cadavers or related human donors, thus providing a much more inexpensive and plentiful source of supply. (On the other hand, telopeptide-containing collagen may also be useful in some instances.)

Incompatibility problems are increased when inductive implants are used, as not only does the matrix need to be acceptably compatible with the host, but also the preparation of any factors which induce cartilage and bone formation. In earlier work, demineralized bone (DMB) was used as part of the implant preparation in order to provide a source of such factors. See, for example, U.S. Pat. Nos. 4,440,750 and 4,430,760. Various attempts have been made to purify, from bone, the factors, presumably protein, which are responsible for osteoinduction. U.S. Pat. Nos. 4,294,753 and 4,455,256 to Urist disclose a bone morphogenic protein (BMP) which is extracted from demineralized bone using urea or guanidine chloride, and then reprecipitated. Further purifications of this factor have been reported by Urist in *Clin Orthop Rel Res* (1982) 162:219; *Science* (1983) 220:680; and *Proc Natl Acad Sci* (USA) (1984) 81:371. The BMP reported by Urist has a molecular weight of 17,500–18,000 daltons and is unadsorbed to carboxymethyl cellulose (CMC) at pH 4.8.

Presumptively different osteogenic factor proteins were isolated from DMB and purified by Seyedin and Thomas (U.S. Pat. No. 4,434,094 and Ser. No. 630,938, filed 16 Jul. 1984, and assigned to the same assignee). The active factor(s) in these preparations are, unlike the Urist factor, adsorbed to CMC at pH 4.8. The preparations were sufficiently purified that xenogeneic hosts could accept them without an immune response.

Attempts have been made to combine sources of an osteoinductive factor with a biocompatible support. U.S. Pat. No. 4,440,750 (supra) discloses a reconstituted atelopeptide collagen preparation in combination with DMB, or a DMB extract. U.S. Pat. No. 4,394,370 to Jeffries discloses the combination of a collagen preparation (which, however, contains the telopeptides), and a crude extract of DMB. The Jeffries disclosure references the BMP of Urist, and while commenting that BMP is not species specific in its activity, exemplifies the use only of allogenic DMB as the starting material for the extract, presumably because of perceived problems with immunogenicity. Also, the Jeffries disclosure requires the use of a minimum of 5% DMB extract by weight in the compositions. The combination with collagen support was apparently not tested in vivo.

Reddi, et al, *Proc Natl Acad Sci* (1983) 69:1601 described the use of allogenic demineralized bone powder to evoke cartilage and bone formation in rat hosts. Sampath, T. K. et al (*Proc Natl Acad Sci* (USA)) have also suggested the combination of allogenic rat bone collagen powder (presumably lacking the osteogenic factor) and a low molecular weight osteogenesis factor (presumably that of Urist) to be effective in bone repair in rat subjects. Thus, while the osteogenesis factor was xenogeneic, the support provided by the conductive portion of the implant disclosed in the Sampath (supra) was allogenic.

Because of supply and cost considerations, it would be advantageous to provide an entirely xenogeneic osteoinductive support implant. In order to do this, it is necessary to provide a support for the effective disposition of an osteogenic protein, wherein both the support and protein are of acceptably low immunogenicity, and wherein the composition is effective in inducing bone growth.

DISCLOSURE OF THE INVENTION

The invention provides an implantable material for inductive bone repair which contains both a chemically defined hypoimmunogenic supporting matrix for bone growth and an effective amount of a hypoimmunogenic purified osteoinductive factor which biochemically promotes the ingrowth of bone. The intermediate formation of cartilagenous tissue also occurs. The compositions of the invention can be utilized for repair of major and minor bone defects whether used for reconstruction, onlays, or for peridontal purposes.

Thus, in one aspect, the invention comprises a composition effective in inducing and supporting bone growth in a subject vertebrate, preferably a mammal, which composition comprises an osteoinductively effective amount of a chondrogenic/osteogenic protein extract (OFE) derived from bone sufficiently free from impurities so as to be hypoimmunogenic, in combination with a hypoimmunogenic carrier preparation containing at least 75% wt/wt of the final composition as mineral carrier. The remaining portion of the carrier preparation can be hypoimmunogenic non-fibrillar or fibrillar collagen; non-fibrillar collagen appears more effective, and is preferred. The mineral component of the carrier is preferably hydroxyapatite (HA), tricalcium phosphate (TCP) or mixtures thereof.

The OFE will ordinarily be present in the amount corresponding to about 0.5-4% of OFE partially purified preparation (as defined below) based on the total composition; the preparations of OFE described are sufficiently pure to be hypoimmunogenic and sufficiently concentrated in activity that a maximum of 4% wt/wt of OFE preparation is required. Preparations of higher purity would, of course, require less to be added.

In other aspects, the invention relates to methods of effecting bone repair in subject vertebrates by implantation of the compositions of the invention.

BRIEF DESCRIPTION OF THE DRAWINGS

FIG. 3A shows the results of histological examination of implants of the invention compositions after 14 days.

FIG. 3B shows the results of histological examination of implants of the invention compositions after 28 days.

FIG. 4 shows the results of proteoglycan assay performed on implants of the invention compositions.

MODES OF CARRYING OUT THE INVENTION

A. Definitions

Figure 1:
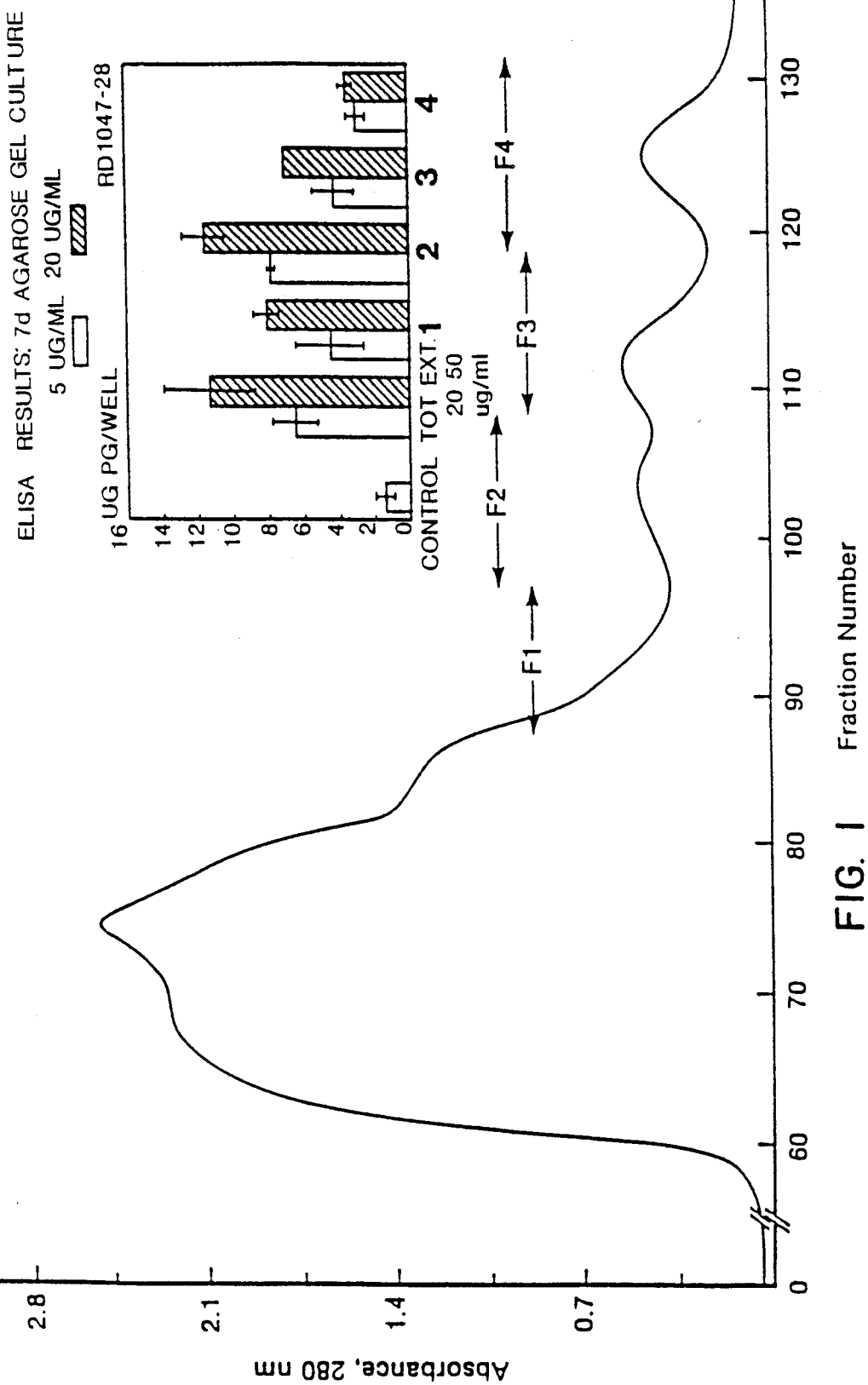
FIG. 1 shows the results of Sephacryl S-200 fractionation of a concentrated, resolubilized extract from DMB. Fraction F2, representing a MW range of 10,000-35,000 daltons contains most of the OFE activity.

As used herein, "osteoinductive" and "osteogenic" are used interchangeably and refer to conversion of bone progenitor cells into living osseous tissue. The induction may result in osteogenesis—i.e., direct formation of mineralized bone through secretion of the organic and inorganic components of bone, or the osteoinduction may also involve intermediate formation of cartilage—i.e., the osteoinductive factor may also be chondrogenic. Indeed, proteoglycan which is diagnostic for cartilage formation, is used as an index of osteoinductive activity of the compositions of the invention.

"Derived from" when referred to the osteogenic factors herein refers to a structural relationship or homology. It is not limited to physical derivation. Thus osteogenic factor "derived from" bone indicates that the factor or factors has an amino acid sequence homologous and similarly functional to those of factors natively produced in bone tissue; it does not necessarily mean that the material used is directly isolated from bone per se. It might, for example, be made synthetically, or by using recombinant DNA techniques.

"Hypoimmunogenic" refers to an acceptable biocompatibility. It is understood that many substances may be immunogenic in some animals and applications but are not able to raise detectable levels of specific immunoglobulins in others. It is also understood that complete absence of specific immunoglobulins and of inflammation may not be required. Thus, when used to described the composition components or the compositions of the invention, "hypoimmunogenic" is functionally defined to mean that any immune responses are within acceptable levels.

"Atelopeptide collagen" refers to collagen which has been suitably treated so as to remove or partially remove the telopeptide, or immunogenic portions. Briefly, and in explanation, collagen comprises a fibrillar structure composed of bundles of triple helical configurations of repeating amino acid sequences. These triple helical sequences are terminated by non-helical structures, "telopeptides" which are responsible both for the cross-linking between various collagen chains, and, in part, for the immunogenicity of collagen preparations. Removal of these structures can be accomplished by treating with suitable proteolytic enzymes such as trypsin. The resulting atelopeptide collagen is more suitable for xenogeneic use, as the major species-specific immunogens have thus been removed.

"Non-fibrillar collagen" has been treated so as not to maintain its native fibrillar structure. This term thus refers to collagen which has been solubilized and has not been reconstituted into its native fibrillar form. The fibrillar construction can be disrupted by dissolution; it can be returned to solid form either by reconstituting the fibers (fibrillar) or by non-specific aggregation (non-fibrillar). Non-fibrillar collagen can also be prepared by denaturation e.g. by heating the fibers with or without first solubilizing them.

The non-fibrillar collagen useful in the invention is used as a solution, as a gel, or as a solid which is non-specifically aggregated after dissolution such as through lyophilization. It must not be reconstituted—i.e., it must not be returned to fibrillar form.

Figure 2:
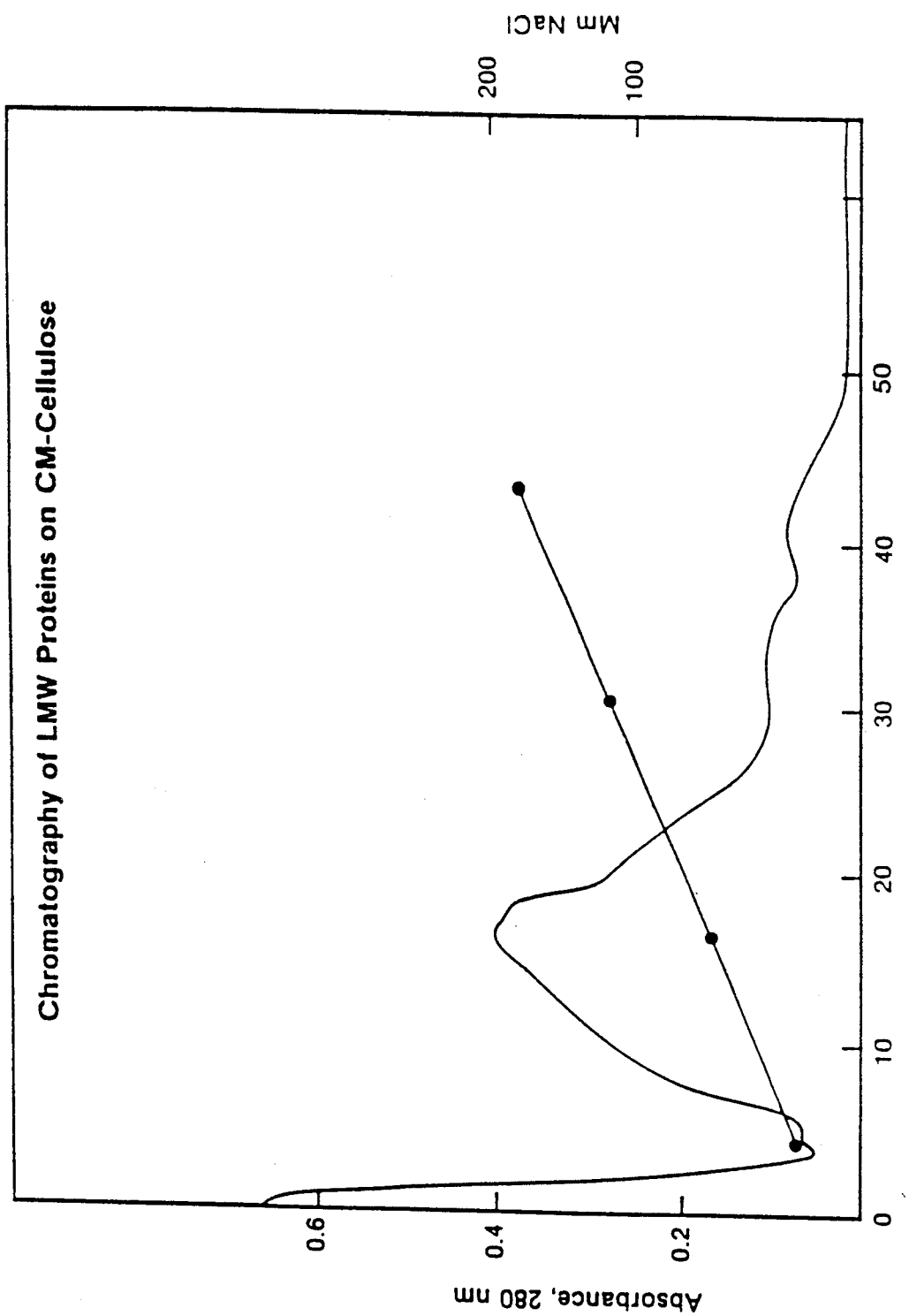
FIG. 2 shows the results of CMC fractionation of the F2 fraction of FIG. 1. The fraction eluting between 50-250 mM NaCl contains the OFE activity.

"OFE" or osteogenic factor extract designated as "partially purified OFE" is defined as the partially purified extracts from bone described hereinbelow which is the <35,000 low MW fraction, either bound to and removed from a cation exchange resin, in a manner similar to that shown in FIG. 2 herein, or treated with and unadsorbed to an anion exchange resin such as DEAE cellulose under the conditions described below. Percentages of OFE in the compositions of the invention are given in terms of the partially purified preparations described. However, it is understood that other methods of preparation which yield comparable amounts of osteogenic activity may also be used, if sufficiently pure to be hypoimmunogenic.

B. General Description

The compositions of the invention are mixtures of effective amounts of an osteoinductive factor (OFE) preparation which is sufficiently purified to be hypoimmunogenic when used xenogeneically, with carrier, wherein the carrier provides at least 75% of the weight of the total composition as mineral, and may include an additional carrier material such as collagen. The percentage of a particular OFE preparation needed in the composition will, of course, depend on the purity of the preparation, but for the preparations described below, a range of 0.5-4% is suitable.

The OFE Preparation

OFE preparations which meet the criterion of sufficient purity to be hypoimmunogenic in xenogeneic hosts may be prepared in several ways. As sources for the factor, bone, dentin, osteosarcomas, or chondrosarcomas and other tissues of vertebrate origin containing OFE can be used. It has been shown that OFE preparations from human, monkey, bovine and rat are non-species specific in their ability to produce endrochondreal bone in xenogeneic implants by Sampath, T. K., et al, *Proc Natl Acad Sci* (USA) (1983) 80:6591. Thus the OFE which is usable in the mixtures of the invention may derive from any of these sources, and, indeed, may be any protein having osteoinductive activity which is substantially similar to those proteins derived from vertebrate sources, whether thus prepared, modified by inadvertent or intentional means, prepared by chemical synthesis, recombinant DNA techniques, or other such procedures. For example, in addition, the bone morphogenic protein of Urist, if purified sufficiently, may perhaps also be used. The OFE must meet the requirements only of substantial similarity to a protein derivable from a vertebrate source, osteoinductive functionality, and acceptably low immunogenicity.

One useful process for preparing the partially purified OFE useful in the compositions of the invention begins by treating porcine or bovine long bone materials (because of ready availability) with mechanical and abrasive techniques to clean and fragment them, and defatting by extraction with organic solvents such as ether or ethyl acetate, and then demineralizing usually by extraction with strong acid using standard techniques, and then using the resulting DMB as a starting material.

To obtain the solubilized OFE, the DMB is then extracted with a chaotropic agent such as guanidine hydrochloride (at least about 4M), urea (8M) plus salt or various other chaotropic agents. The extraction is preferably carried out at reduced temperatures in the presence of protease inhibitors to reduce the likelihood of digestion or denaturation of the extracted protein, for about 4 hr-1 day. After extraction, the extractant may be removed by suitable means such as dialysis against water, controlled electrophoresis, or molecular sieving or any other suitable means. The extract, with or without the extractant removed, is then subjected to gel filtration or other sizing procedure to obtain fractions of molecular weight below about 35,000 daltons using standard techniques.

The low molecular weight fraction is freed from competing ions and is then subjected to ion exchange chromatography using either cation exchange, for example with CMC at approximately pH 4.5–5.2, preferably about 4.8 in the presence of a non-ionic chaotropic agent such as urea; or using anion exchange, for example, with DEAE cellulose, in the presence of, for example, 6M urea and 20 mM sodium phosphate at approximately pH 7.2.

The OFE is adsorbed to the cation exchange resin, and is eluted under suitable conditions; the active eluate fractions resulting from the cation exchange chromatography may be used directly in the compositions of the invention, and are defined as "partially purified".

Alternatively, the non-adsorbed material resulting from subjecting the low MW fraction to treatment by anion exchange resin contains the OFE activity, and this non-adsorbed protein, after dialysis to remove urea, may also be used as a "partially purified OFE". The protein in the anion exchange resin treated solution can be recovered by lyophilization, or stabilized by dialyzing against 0.01N HCl.

The OFE-containing solution or solid obtained from either method of preparation may also, if desired, be further purified; this is an optional step. Specific details of illustrative methods for thus purifying the OFE proteins to a satisfactory level, are set forth below. The percentage compositions are given in terms of OFE partially purified to these levels; of course, correspondingly smaller amounts of more highly purified OFE would be used.

The Carrier

The carrier portion of the preferred composition provides at least 75%, preferably around 85-95%, of a mineral component to the composition and an additional component selected from fibrillar or non-fibrillar collagen or both. One additional workable embodiment uses a carrier comprising bone collagen powder (85-95%) and non-fibrillar collagen (5-10%).

The mineral component is generally selected from various forms of calcium phosphate, preferably hydroxyapaptite (HA) and tricalcium phosphate (TCP) or most preferably, mixtures thereof. Both HA and TCP are commercially available, and selection can be made from a number of mesh sizes and porosities. These materials have been disclosed to be useful in the construction of hard tissue implants and are thus of suitable biocompatibility to comprise a portion of the composition of the invention. See, e.g. U.S. Pat. No. 4,314,380 which discloses HA preparations, and Hayashi, K. et al *Arch Orthop Traumat Surg* (1982) 99:265 which discloses an alternate form of HA.

An attribute of the compositions of the invention is acceptably low immunogenicity. Accordingly it is preferable in general to use the atelopepetide forms of non-fibrillar or fibrillar collagen components. There may, however, be instances in which the presence of telopeptides, due to the configuration of the implanted composition, the susceptibility of the host, or some other reason, is not sufficiently detrimental to the hypoimmunogenicity to render the composition unacceptable. In other words, the use of atelopeptide collagens is preferred, but not necessarily required.

The non-fibrillar collagen used can be supplied as a collagen in solution, as a lyophilized form of collagen in solution which is thereby non-specifically aggregated, as a gelatin carrier or as mixtures of the foregoing. A preferred source of the non-fibrillar collagen is collagen in solution (CIS) which is obtainable under the trademark Zygen ® from Collagen Corporation, Palo Alto, Calif. However, any non-reconstituted collagen preparation may be used.

The non-fibrillar collagen must be present in an amount of at least approximately 5% in the composition if only BCP, and no mineral component is used. It may constitute the entire collagen component of the composition either in the presence or absence of mineral.

For those compositions which contain over 75% ceramic, fibrillar collagen may be used in lieu of, as well as in addition to, the non-fibrillar form, though these embodiments are not preferred. The fibrillar collagen can be derived from various sources, and a number of fibrillar collagen preparations are available in the art, wherein collagen derived from bone or skin of various mammals has been solubilized or dispersed in liquid medium and then recovered in fibrillar form. Preparations wherein the collagen is reconstituted into fibers include, for example, Zyderm ® collagen implant (ZCI), available from Collagen Corporation, Palo Alto, Calif. Other fibrillar preparations, include Avitene ®, which represents dispersed fibers that still have native fibrillar form; and Collagenfleece ® which is a dispersed preparation subsequently freeze dried. (These latter preparations are not, therefore, "reconstituted".)

A collagen preferred as a majority constituent in non-mineral preparations is bone collagen powder (BCP). A preparation of BCP is described in detail in U.S. Ser. No. 752,447, filed 5 Jul. 1985 now pending, and assigned to the same assignee, incorporated herein by reference; a suitable preparation is also illustrated below.

Preparation of the Compositions

In a typical protocol, a small amount of the OFE solubilized in dilute acid is combined with one of the carrier components and incubated at low temperature with stirring. The mixture may be lyophilized, if desired, and additional components supplied as solids, or as solutions or suspensions. If the final addition is as a solution or suspension, this final addition may also be followed by lyophilization. For example, the OFE may be mixed first with collagen in solution, the incubated mixture lyophilized, and the mineral component added to the lyophilized mixture to form a dry final product. Or, the mineral component may be added directly to the OFE, followed by addition of a collagen solution or suspension, and the resulting mixture lyophilized.

In one suitable alternate protocol, non-fibrillar collagen is supplied as a solution, such as CIS, or as gelatin and is mixed, if desired with an additional component, such as for example, BCP or other biocompatible material. The resulting mixture is mixed with the purified OFE-containing preparation and stirred in dilute mineral acid, e.g., 0.01N HCl, for 1-2 hr at low temperature, roughly 4° C. The mixture is then dialyzed against water at a pH below about 5 and lyophilized to obtain a solid material. The solid material may also be supplemented with additional compatible substances. Since certain ceramic materials, such as HA, would dissolve in the course of this process, they must be added after lyophilization.

The resulting solid material may be hydrated with comparable volumes of, for example, saline solution and extruded or otherwise mechanically treated to obtain an implant with the desired properties. The physical properties of the implant material are variable by appropriate modifications of the foregoing protocols and by adjusting the nature and amount of the supplemental carrier material. Thus the compositions may be in the form of powders, sheets, or rigid solid, such as a block or rod. The solid material can be formed into implants appropriate to uses in the repair of bones, either as onlay grafts, in bone reconstruction, in the treatment of fractures and in other orthopedic indications. The methods for utilizing solid compositions to form such implants, and surgical methods for implanting them, are well understood in the art, and the compositions of the invention are useful in employing these standard means.

When placed in the desired location, the implant composition provides a matrix for the ingrowth of new cartilage and bone, as well as stimulating the production of these materials by virtue of the presence of an osteoinductive factor.

Use of the Compositions

The compositions of the invention are used in a manner generally known in the art to repair major or minor defects in bone caused by trauma, disease, or congenital defects.

The compositions can also be used in conjunction with metal prostheses, such as those made of aluminum, or of alloys. U.S. Pat. No. 3,820,167, e.g., describes a prosthesis fabricated of titanium or an alloy thereof. The composition of the invention serves to close any gaps between the prosthesis and surrounding bone, and thus to secure the prosthesis more firmly in place.

As described in the specific examples below, these compositions when implanted subcutaneously in xenogeneic hosts, are capable of stimulating bone tissue formation. Their capacity to do so can be verified by explanting the composition, and assessing the explant histologically, for cartilage proteoglycan formation, for the presence of calcium and for the presence of alkaline phosphatase. (Cartilage proteoglycan is a measure of cartilage formation; alkaline phosphatase is a marker of calcifying hypertrophic cartilage.) In addition, the host organism is shown to be free from antibodies reactive against the implanted material.

C. Examples

The following examples are intended to illustrate the invention. Alternative methods for preparing the components of the composition and for preparing the composition itself are within the scope of the invention, provided the resulting composition falls within the scope of the appended claims.

EXAMPLE 1

Preparation of Partially Purified OFE

Preliminary Extraction and Purification

The fraction F2 as set forth below can be used in several alternative ways; it can be subjected to cation exchange chromatography and the collected combined fractions having OFE activity used as the partially purified OFE preparation in the composition of the invention. Fractions F1 and F3 also contain some OFE activity. (These fractions can be subjected to further purification by, for example, reverse phase HPLC or gel electrophoresis.) Alternatively, the material represented by fraction F2 may also be subjected to treatment with anion exchange resin treatment, and the non-adsorbed solution can be used in the compositions of the invention, or this too can be further purified in a manner analogous to the cation exchange eluate. Thus, in general, according to the purification techniques illustrated, sufficient purification is obtained to provide suitable preparations by a combination of extraction with chaotropic agent, size-separation, and subsequent treatment with either DEAE or CMC. Further purification steps are then optional.

Preparation of Demineralized Bone (DMB)

Fresh bovine metatarsal bone was obtained from the slaughterhouse and transported on dry ice. The bones were cleaned of marrow and non-bone tissues, broken into fragments smaller than 1 cm diameter, and pulverized in a mill at 4° C. The pulverized bone was washed twice with 9.4 liters of double distilled water per kg of bone for about 15 min each wash, and then washed overnight in 0.01 N HCl at 4° C. Washed bone was defatted using 3×3 volumes ethanol, followed by 3×3 volumes diethyl ether, each wash for 20 min, and all at room temperature. The resulting defatted bone powder was then demineralized in 0.5 N HCl (25 l/kg defatted bone) at 4° C. The acid was decanted and the resulting DMB washed until the wash pH was greater than 4, and the DMB dried on a suction filter.

Extraction of Noncollagenous Proteins

The DMB as prepared above was extracted with 3.3 liters of 4M guanidine-HCl, 10 mM ethylenediaminetetraacetic acid (EDTA), pH 6.8, 1 mM PMSF, 10 mM NEM per kg for 16 hr, the suspension suction filtered and the non-soluble material extracted again for 4 hr. The soluble fractions were combined and concentrated at least 5-fold by ultrafiltration using an Amicon ultrafiltration (10K) unit, and the concentrate dialyzed against 6 changes of 35 volumes cold deionized water over a period of 4 days, and then lyophilized. All of the procedures of this paragraph were conducted at 4° C. except the lyophilization which was conducted under standard lyophilization conditions. In some cases the concentrated extract from ultrafiltration was used directly in the gel filtration step.

Gel Filtration

The ultrafiltration concentrated extract or the lyophilized material from above, redissolved in 4M guanidine-HCl, was fractionated on a Sephacryl S-200 column equilibrated in 4M guanidine-HCl, 0.02% sodium azide, 10 mM EDTA, pH 6.8. Fractions were assayed by their absorbance at 280 nm and for chondrogenic activity by ELISA (Seyedin et al. *J. Cell Biol* (1983) 97:1950) and the fractions were combined as shown in FIG. 1. Fraction F2 of FIG. 1, constituting a low molecular weight (LMW, 10,000–35,000 daltons) protein fraction possessing the greatest activity was dialyzed against 6 changes of 180 volumes of deionized water and lyophilized. All operations except lyophilization were conducted at room temperature.

Cation Exchange Chromatography

Fraction F2 from above was dissolved in 6M urea, 10 mM NaCl, 1 mM NEM, 50 mM sodium acetate, pH 4.8 and centrifuged at 10,000 rpm for 5 min. The supernatant was fractionated on a CM52 (a commercially available CMC) column equilibrated in the same buffer. The column was eluted using a 10 mM to 400 mM NaCl gradient in the same buffer, and fractions collected and combined based on their absorbance at 280 nm as shown in FIG. 2. The eluate between 50–250 mM NaCl was dialyzed against 6 changes of 110 volumes of deionized water for 4 days and lyophilized. All of the foregoing operations were conducted at room temperature except dialysis (4° C.). The lyophilized eluate is a partially purified OFE according to the definition herein.

Purification by Treatment with Anion Exchange Resin

The fraction F2 representing low molecular weight proteins was dissolved in buffer containing 6M urea, 20 mM sodium phosphate, pH 7.2, 20 mM NaCl, and protease inhibitors. The solution was then run over a DEAE cellulose column equilibrated with the same buffer. The flow-through fraction, which contains the OF, was dialyzed against water to remove urea, and the OFE recovered by lyophilization. Alternatively, the flow-through volume was dialyzed against 0.01 NHCl, and stored in 0.01 NHCl at a protein concentration of 1–10 mg/ml. The foregoing solution was stable over a period of several months. The lyophilized or unlyophilized dialyzates are partially purified OFE according to the definition herein.

EXAMPLE 2

Preparation of the Inductive Compositions with no Mineral Content

Non-fibrillar collagen may be provided in commercial form by utilizing Zygen®, collagen in solution (CIS) which is commercially available. This is an atelopeptide form of solubilized collagen having a pH of approximately 2.

A. Non-fibrillar Collagen Only

To prepare a composition containing only non-fibrillar collagen in admixture with the partially purified OFE, CIS at 1–3 mg/ml in 0.01N HCl was mixed with partially purified OFE (by anion exchange treatment, as described above) also dissolved in 0.01N HCl to give an amount of approximately 2.5% in the final composition, and stirred for 1–2 hr at 4° C. The mixture was dialyzed against water and then lyophilized.

B. Non-Fibrillar Collagen Plus BCP

To prepare a composition containing only a small percentage of non-fibrillar collagen, CIS at a concentration of 1–3 mg/ml was mixed with bone collagen powder (BCP) (prepared as described in U.S. Ser. No. 752,447 (supra), incorporated herein by reference) to give a final concentration of collagen contributed by CIS as 5% by weight of total collagen. To this mixture was added OFE, partially purified by anion exchange resin treatment as set forth above, to give 2.5% of the total composition as OFE by weight on a solids basis. This mixture was stirred to 1–2 hr at 4° C., dialyzed against water and lyophilized.

EXAMPLE 3

Assay of Inductive Implants

Implantation

The lyophilized materials prepared in B of Example 2 were rehydrated in 2 parts by weight of sterile water. The rehydrated materials were made into pellets weighing approximately 80–100 mg wet. The pellets were put into gelatin capsules and the capsules implanted subcutaneously in the ventral thoracic region of male rats. Each rat received two implants of the same material on lateral sides, and explants for testing were removed at 14 and 28 days. The explants were assayed by histology, by assay for alkaline phosphatase activity and for metal ions, and for cartilage proteoglycans.

The sera of the implanted rats were also examined for circulating antibodies against the implants.

Non-immunogenicity of the Implants

Sera were removed from the implanted animals after 28 days, and assayed for the presence of antibodies against the implanted material using an enzyme linked immunosobent assay (ELISA) technique; Microtiter wells were coated with 2–5 g of each of the components of the composition in 20 mM carbonate buffer (100 1) pH 9.6 at 4° C. overnight. The wells were washed 3 times with PBS containing 0.05% Tween 20 surfactant so as to remove unbound antigen. The rat sera were then added for 2 hr at room temperature, and the wells washed 3 times with PBS-Tween 20 surfactant. Goat anti-rat IgG conjugated with horseradish peroxidase (1:2000 dilution) was added, and the wells incubated for 1.5-2 hr at room temperature. Unbound labeled antibody was then removed with PBS-Tween 20 with surfactant, and peroxidase substrate was added. The plates were incubated at room temperature for 30 min, and the plates then scanned for optical density.

Antibodies were not detected in any of the rats whose sera were tested, even using undiluted sera. Controls consisted of sera from rats injected with crude extract from DMB (i.e. unfractionated material) which were positive in the ELISA technique used, and gave high antibody titers.

Characterization of Explants-Histology

Explants which had been removed after 7, 14, and 28 days were subjected to histological assessment by fixing in 10% neutral formalin for 26 hr, and then processing for paraffin embedding. 4-6 micron sections were taken from the imbedded tissues and were subsequently stained with either hematoxylin-eosin or with Saphranin-O. Saphranin-O is selective for cartilage proteoglycan. All of the explanted material indicated the presence of cartilage proteoglycan by this technique.

Assay for Extractable Bone Components 6 rats were implanted with the matrix prepared in ¶B of Example 2 and, as negative controls, 6 rats were implanted with a similar matrix which did not contain OFE. Explants were removed after 14 and 28 days. The 14-day explants were extracted prior to analysis for proteoglycan, and for alkaline phosphatase as set forth below; the 28 day explants were used for determination of calcium ion.

Formation of Proteoglycan

Cartilage proteoglycan was assayed by an ELISA technique. The explants were weighed immediately after removal and frozen at $-70°$ C. until extraction. For the extraction, the explants were cut into slices, and homogenized in ice cold extraction buffer in a Tekmar Tissuemizer for two 30 sec bursts at maximum setting. The extraction buffer was 6M guanidine hydrochloride, 75 mM sodium acetate or 4M guanidine hydrochloride, 50 mM acetate both containing 20 mM EDTA, 1 mM PMSF and 10 mM NEM at pH 5.8. Buffer was used in a volume equal to the weight of the explant extracted, and the samples were incubated overnight (20 hr) at 4° C. The samples were then centrifuged at 12,000 rpm for 1 hr at 4° C., and the supernatants dialyzed overnight at 4° C. against 50 volumes of 50 mM Tris, 200 mM NaCl, pH 7.4. The dialyzate was subjected to ELISA performed as described by Rennard, et al, *Arch. Biochem Biophys* (1980) 207:399 and by Seyedin, S., et al, *J. Cell Biol* (1983) 97:1950 using polystyrene microplates (Flow Laboratories, McClean, Va.). The antisera and the proteoglycan standard were prepared from Swarm rat chondrosarcoma tissue as described by Seyedin, S., et al, (supra). Horseradish peroxidase conjugated goat anti-rabbit IgG was used as the second antibody, samples were assayed in different solutions in PBS 0.05%, Tween 20, 1 mg/ml BSA and quantitated by use of the inhibition ELISA described by Shuures, et al, *Clin Chim* (1977) 81:1.

Explants which had contained OFE showed a proteoglycan content of $490\pm30$ mg/g wet tissue; explants which had contained no OFE showed only $35\pm5$ mg/g wet tissue.

Extractable Calcium

The formation of bone was also assessed by determination of calcium. The explants were cut in small pieces and suspended in 1:10 (m/v) and 1:20 (m/v) of 0.5N HCl to dissolve the ions. The samples were incubated for another 5 days at room temperature and centrifuged at 12,000 rpm for 40 min. The calcium concentration of the supernatant was determined by atomic adsorption (Trace Analysis Laboratory, Hayward, Calif.); and found to be $30\pm5$ mg/g wet tissue.

Analysis for Alkaline Phosphatase

To determine alkaline phosphatase (AP), the explants were cut in small pieces and homogenized in 3 ml ice cold 1.5M NaCl, 3 mM NaHCO$_3$, pH 7.5. The homogenized samples were then centrifuged at 12,000 rpm for 50 min at 4° C., and an aliquot of the supernatant diluted 1:10 in cold distilled water. The method of Huggins, et al, *J Exp Med* (1961) 114:761 was used to assess alkaline phosphatase using polystyrene plates. Explants which had orginally contained OFE showed $17\pm5$ units of AP per gram of wet tissue, explants which contained no OFE showed no AP activity.

EXAMPLE 4

Preparation of Mineral-Containing Compositions and of R-DBP

OFE partially purified using the anion exchange treatment of Example 1 was used as a 3 mg/ml solution in 0.01N HCl.

Preparation of OFE/NFC/Ceramic

A 5.4 ml sample of the OFE solution was stirred with 22 ml Zygen ® CIS (65 mg protein) at 4° C. for 5 min; 569 mg of HA/TCP, obtained from Zimmer Corp, Warsaw, IN, was added and the mixture incubated at 4° C. for 5 min, and then lyophilized. The resulting solid was 87.5% ceramic, 10% non-fibrillar collagen (NFC), 2.5% OFE; all percentages representing solids by weight. A control preparation was made identically, but using 0.01N HCl instead of OFE solution.

Preparation of OFE/FC/Ceramic

A 5.4 ml sample of the OFE solution was stirred with 569 mg of HA/TCP, obtained from Zimmer Corp, Warsaw, IN, at 4° C. for 5 min and then lyophilized. The resulting solid was mixed with 0.6 ml of 65 mg/ml Zyderm ® collagen implant (fibrillar collagen). The resulting solid was 91.5% ceramic, 6% fibrillar collagen (FC), 2.5% OFE; all percentages representing solids by weight. A control preparation was made identically, but using 0.01N HCl instead of OFE solution.

Preparation of R-DBP

For comparison purposes, a composition designated reconstituted demineralized bone powder (R-DBP) was also prepared.

A 5.4 ml sample of the OFE solution was stirred with 22 ml Zygen ® CIS (65 mg protein) and 569 mg of BCP, prepared as set forth above, at 4° C. for 5 min; and then lyophilized. The resulting solid was 87.5% BCP, 10% non-fibrillar collagen (NFC), 2.5% OFE; all percentages representing solids by weight.

EXAMPLE 5

Assessment of Mineral-Containing Compositions

Implantation

The OFE/NFC/Ceramic was hydrated in 0.5 volumes of sterile saline, allowed to soak for 5 min, and packed into a 1 cc syringe. The sample was extruded, dried for about 1 hour, and cut into 100 mg pellets. The corresponding control without OFE was prepared for implantation identically.

For OFE/FC/Ceramic, the FC used in the preparation served as the hydrating medium. The mixture as prepared in Example 4 was air dried, compacted, and pelleted into 100 mg pellets. The corresponding control without OFE was prepared for implantation identically.

The R-DBP was hydrated in 2 volumes of sterile saline, allowed to soak for 45 min at room temperature, and packed into a 1 cc syringe. The sample was extruded, dried for about 1 hour, and cut into 100 mg pellets.

All samples were implanted subcutaneously on the ventral thoracic region of 30-34 day old male Sprague-Dawley rats. Explants were removed at 14 and 28 days and examined for cartilage and bone induction as described below.

Histological Examination

The results of histological examination of the explants are shown in FIG. 3. All samples containing OFE showed some bone formation after 28 days, while those not containing this factor did not. After 14 days, the cartilage and bone formation was concentrated in microfocal areas, ranging from trace to moderate amounts. By 28 days, there was good bone formation and marrow differentiation. The presence of NFC in the composition appeared to accelerate bone ingrowth.

Cartilage Formation

Cartilage formation was measured by proteoglycan assay as described in Example 3. The results of these assays after 14 days are shown in FIG. 4. The OFE/NFC/Ceramic composition gave 1.6 mg/g wet tissue, followed by R-DBP which gave 0.8 mg/g. The remaining compositions gave smaller amounts, but that for OFE/FC/Ceramic exceeded the controls.

Bone Formation

Figure 5A:
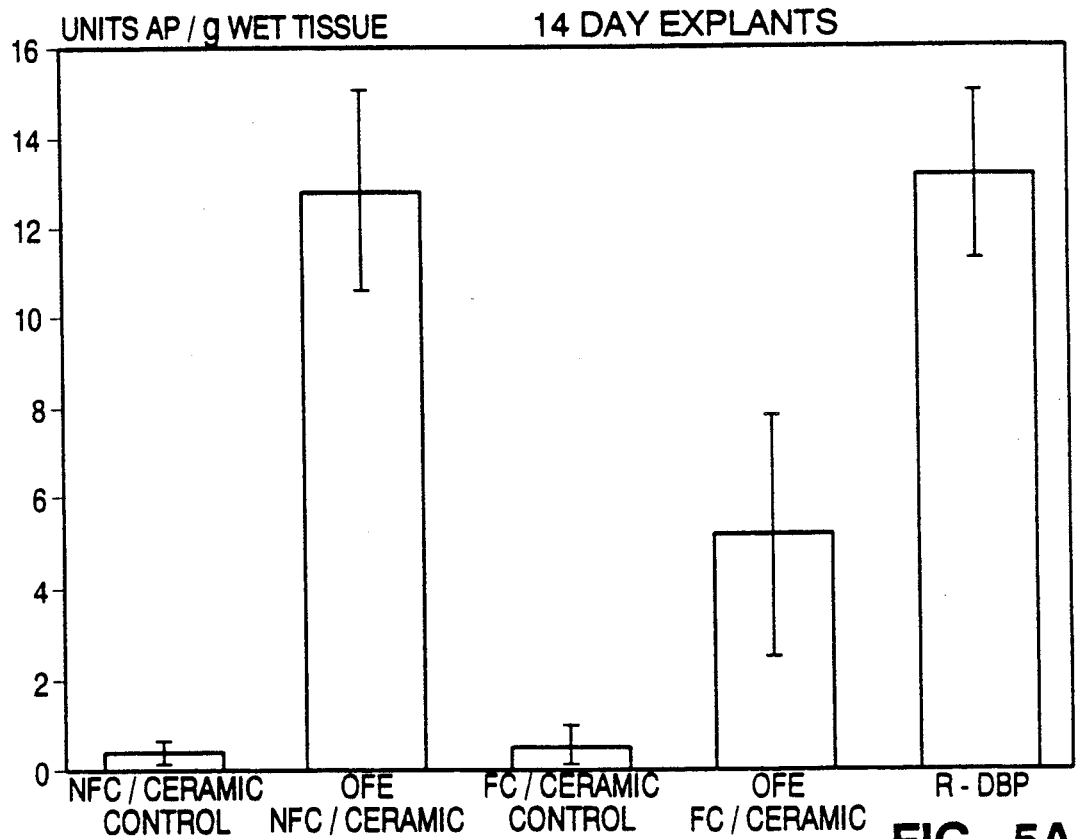
FIG. 5A shows the results of alkaline phosphatase assay of explants of the invention compositions after 14 days.
Figure 5B:
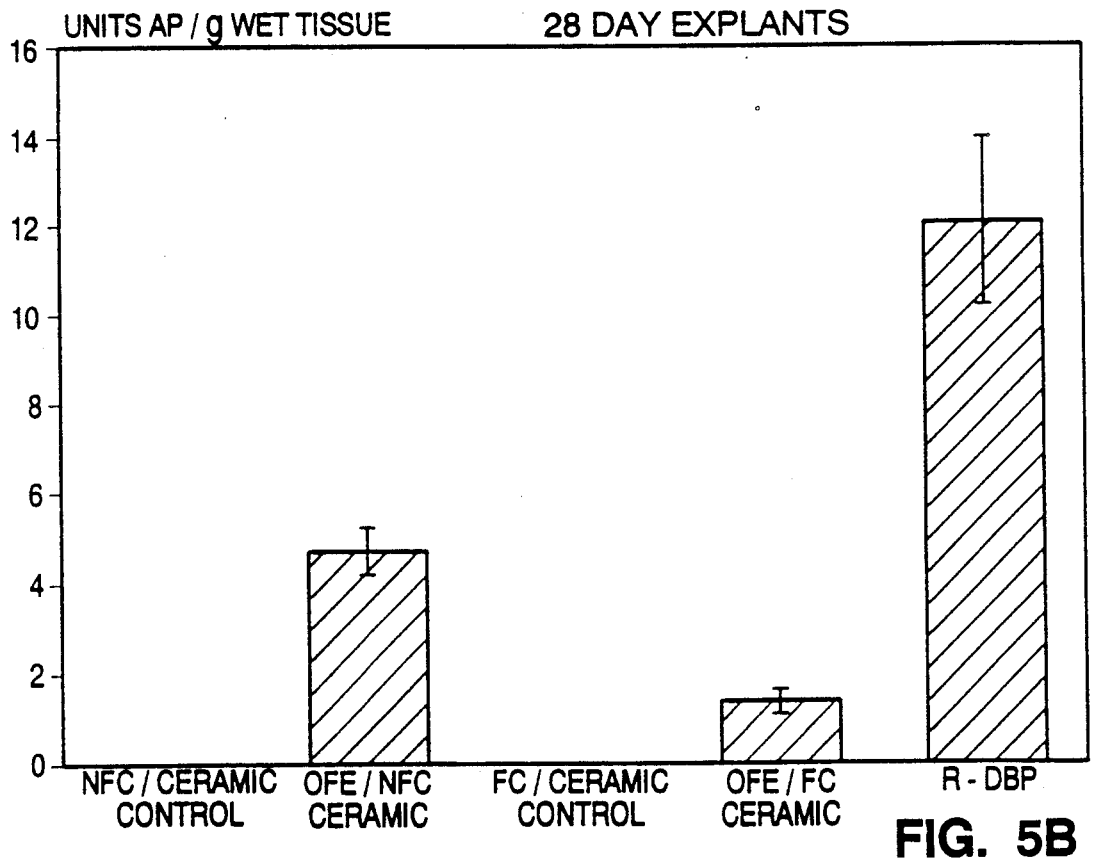
FIG. 5B shows the results of alkaline phosphatase assay of explants of the invention compositions after 28 days.

Bone formation was measured by alkaline phosphatase activity, as described in Example 3. These results are shown in FIG. 5. All of the OFE containing compositions gave high levels of AP activity after 14 days; again the NFC-containing compositions were superior. After 28 days, all levels had decreased, as would be expected during the completion of the bone formation process.

We claim:

1. A method of effecting bone repair in vertebrates in need of such treatment which comprises implanting into a bone defect a hypoimmunogenic composition which comprises an osteoinductively effective amount of a protein osteoinductive factor (OFE) derived from bone, which OFE is sufficiently pure to be hypoimmunogenic in a xenogeneic host, said composition containing at least 75% by weight of mineral carrier.

2. A method of effecting bone repair in vertebrates in need of such treatment which comprises implanting into a bone defect a hypoimmunogenic composition which comprises an osteoinductively effective amount of a protein osteoinductive factor (OFE) derived from bone, which OFE is sufficiently pure to be hypoimmunogenic in a xenogeneic host, which composition is 85-95% mineral carrier, 5-15% atelopeptide collagen, and wherein the amount of OFE corresponds to that obtained by including between about 0.5% and 4% by weight of the implant of partially purified OFE.

3. A method of effecting bone repair in vertebrates in need of such treatment which comprises implanting into a bone defect a hypoimmunogenic composition which comprises an osteoinductively effective amount of a protein osteoinductive factor (OFE) derived from bone, which OFE is sufficiently pure to be hypoimmunogenic in a xenogeneic host, which composition is 87.5% TCP/HA mixture and 10% non-fibrillar collagen, and wherein the amount of OFE corresponds to that obtained by including 2.5% by weight of the implant as partially purified OFE.

4. A method of effecting bone repair in vertebrates in need of such treatment which comprises implanting into a bone defect a hypoimmunogenic composition which comprises an osteoinductively effective amount of a protein osteoinductive factor (OFE) derived from bone, which OFE is sufficiently pure to be hypoimmunogenic in a xenogeneic host, which composition is 91.5% TCP/HA mixture and 6% reconstituted fibrillar collagen, and wherein the amount of OFE corresponds to that obtained by including 2.5% by weight of the implant as partially purified OFE.

5. The method of claim 1 wherein the mineral carrier is selected from TCP/HA and mixtures thereof.

6. The method of claim 1 wherein the amount of OFE corresponds to that obtained by including between about 0.5% and 4% by weight of the implant of partially purified OFE.

7. The method of claim 2 wherein the mineral carrier is selected from TCP/HA and mixtures thereof.

8. The method of claim 2 wherein the atelopeptide collagen is nonfibrillar collagen.

9. The method of claim 2 wherein the atelopeptide collagen is reconstituted fibrillar collagen.

10. The method of claim 3 wherein the collagen is atelopeptide collagen.

11. The method of claim 4 wherein the collagen is atelopeptide collagen.

* * * * *